(12) United States Patent
Igwebuike et al.

(10) Patent No.: US 9,770,370 B2
(45) Date of Patent: Sep. 26, 2017

(54) ADHESIVE WOUND DRESSING

(71) Applicant: Coloplast A/S, Humlebaek (DK)

(72) Inventors: Henning Igwebuike, Lynge (DK);
Grazyna Hansen, Frederiksberg C
(DK); Jan Marcussen, Taastrup (DK)

(73) Assignee: Coloplast A/S, Humlebaek (DK)

( * ) Notice: Subject to any disclaimer, the term of this patent is extended or adjusted under 35 U.S.C. 154(b) by 434 days.

(21) Appl. No.: 14/348,054

(22) PCT Filed: Sep. 28, 2012

(86) PCT No.: PCT/DK2012/050362
§ 371 (c)(1),
(2) Date: Mar. 28, 2014

(87) PCT Pub. No.: WO2013/044924
PCT Pub. Date: Apr. 4, 2013

(65) Prior Publication Data
US 2014/0243728 A1  Aug. 28, 2014

(30) Foreign Application Priority Data
Sep. 30, 2011 (DK) .................. 2011 00752

(51) Int. Cl.
*A61F 13/02* (2006.01)
(52) U.S. Cl.
CPC ........ *A61F 13/0213* (2013.01); *A61F 13/025* (2013.01); *A61F 13/0246* (2013.01); *A61F 13/0253* (2013.01); *A61F 13/02* (2013.01); *A61F 13/0203* (2013.01)

(58) Field of Classification Search
CPC ...... A61F 13/00; A61F 13/02; A61F 13/0203; A61F 13/0213; A61F 13/0246; A61F 13/025; A61F 13/0253
USPC ......................................... 602/41–43, 54–56
See application file for complete search history.

(56) References Cited

U.S. PATENT DOCUMENTS

| 4,231,369 | A | 11/1980 | Sorensen et al. |
| 4,367,732 | A | 1/1983 | Poulsen et al. |
| 4,867,748 | A | 9/1989 | Samuelsen |
| 5,133,821 | A | 7/1992 | Jensen |
| 5,643,187 | A | 7/1997 | N.ae et al. |
| 5,714,225 | A | 2/1998 | Hansen et al. |

(Continued)

FOREIGN PATENT DOCUMENTS

| JP | 2006507065 T2 | 3/2006 |
| JP | 2008178710 T2 | 8/2008 |

(Continued)

*Primary Examiner* — Keri J Nelson
(74) *Attorney, Agent, or Firm* — Coloplast Corp.; Nick Baumann

(57) ABSTRACT

A wound dressing comprising an adhesive layer having a skin-facing surface and a non-skin-facing surface, the non-skin-facing surface being provided with a backing layer, the dressing comprises a central portion comprising an absorbent adhesive, and an border portion surrounding the central portion, wherein the skin facing surface of edge portion of the adhesive layer is continuous and the skin facing surface of central portion is interrupted by interconnected cavities. The cavities provide a storage room and distribution center for wound exudates enabling the dressing to be applied to fast exuding wounds.

14 Claims, 1 Drawing Sheet

(56) References Cited

U.S. PATENT DOCUMENTS

2005/0059918 A1    3/2005  Sigurjonsson
2010/0168635 A1*  7/2010  Freiding ................ A61F 13/02
                                                            602/55

FOREIGN PATENT DOCUMENTS

| | | |
|---|---|---|
| JP | 2009534057 T2 | 9/2009 |
| WO | 0160296 | 8/2001 |
| WO | 2004047695 A1 | 6/2004 |
| WO | 2007121744 A1 | 11/2007 |
| WO | 2010135645 | 11/2010 |

* cited by examiner

ADHESIVE WOUND DRESSING

FIELD OF THE INVENTION

The present invention relates to an adhesive dressing for application to the skin or a wound.

BACKGROUND

Wound dressings comprising a backing layer and a layer of hydrocolloid adhesive are well known, such dressings may be known as hydrocolloid dressings. Whereas these dressings are excellent for application to blisters or slowly exuding wounds, they may be difficult to attach to fast exuding wounds, such as a bleeding wound or scratch. Hydrocolloid adhesive is capable of absorbing large amounts of moisture, but not instantaneously as their initial absorption is low.

Typically, the hydrocolloid dressings have a continuous surface against the skin or wound which does not absorb liquid instantaneously. This leads to the issue of small drops of fluid being squeezed across the surface of the dressing during application of the dressing to the wound and this fluid may be squeezed all the way to the edge of the dressing leading to poor adhesion and premature detachment.

There have been different attempts to solve this problem:

One approach is to optimize the adhesive to a faster initial absorption, e.g. by increasing the amount of hydrocolloid. However, the increase in hydrocolloid may lead to a decrease in adhesive tack and thereby a shorter wear time for the wound dressing. Thus, the increase in absorption rate required to deal with the fluid production rate is not compatible with a well adhering hydrocolloid dressing.

Another way is to provide the wound dressing with an absorbent center zone, such as a pad of an absorbent material, such as a gauze or foam or cellulosic material. This will add an extra step in the production and the resulting product may be more visible and less flexible. Furthermore, adding an absorbent pad fundamentally changes the nature of the hydrocolloid dressing as the benefits of having the hydrocolloid adhesive over the wound bed will not be present anymore.

A third way may be to increase the permeability of the dressing, e.g. by providing adhesive-free zones, by pattern coating the adhesive layer to the backing layer. The pattern may be in the form of a dot-shaped pattern coated on backing film allowing increased vapor permeability at the uncoated areas. However, water infiltration or leakage is possible via the interconnected uncoated areas or channels, which are defined between the discrete dots of adhesive.

EP 806 210 discloses an adhesive wafer, in which the adhesive layer of the wafer is composed of a hydrocolloid-containing skin barrier material. The adhesive layer is embossed to provide a pattern of discrete, non-connecting depressions separated and isolated from each other. The structure facilitates less skin stripping during multiple replacements of the wafer as well as the non-connected structure of depressions reduces the risk of leakage.

SUMMARY OF THE INVENTION

One aspect of the present invention is to provide wound dressing being capable of handling fast exuding wounds.

DETAILED DISCLOSURE

The invention relates to a wound dressing comprising an adhesive layer having a skin-facing surface and a non-skin-facing surface, the non-skin-facing surface being provided with a backing layer, the dressing comprises a central portion comprising an absorbent adhesive and an adhesive border portion surrounding the central portion, wherein the skin facing surface of the border portion of the adhesive layer is continuous and the skin facing surface of central portion is interrupted by a network of interconnected cavities.

The wound dressing of the invention facilitates increased liquid handling capacity by:
a) Increasing the absorption rate of the wound dressing by spreading liquid to a larger area of the absorbent adhesive surface=faster absorption
b) Providing a reservoir for liquid to be stored in the wound dressing until it can be absorbed.

Prior solutions are typically focused on leading the fluid away from the wound in vertical direction, towards the backing layer, thereby avoiding the fluid to spread and macerate the skin. In the present invention, the fluid is distributed horizontally into the interconnected network of cavities, facilitating a faster absorption due to exposure to a larger surface of the absorbent adhesive and the exudates may be absorbed before maceration occurs.

The exudates to be absorbed by the dressing may be liquid or fluid such as blood, wound exudates or other fluids from a wound/skin such as fluid from a blister.

By absorbent adhesive is meant that the adhesive layer of the central portion may comprise hydrocolloid particles or super absorbent particles or fibers. The presence of hydrocolloid in the adhesive provides a good environment for moist wound healing as well as for other skin conditions. By incorporating an amount of hydrocolloid in the adhesive, the wound dressing is able to handle moisture in most conditions.

The adhesive layer of the border portion may be any suitable skin-friendly adhesive. The adhesive may be non-absorbent or it may comprise absorbent particles. In one embodiment, the adhesive of the border portion is the same adhesive as the adhesive of the central portion, i.e. the adhesive of the central portion and the adhesive of the border portion being an integral unit.

Suitable hydrocolloids for the dressing of the present invention include synthetic polymers prepared from single or multiple monomers, naturally occurring hydrophilic polymers or chemically modified naturally occurring hydrophilic polymers. The hydrocolloid polymers may be linear or cross-linked. This include natural or chemically modified natural polymers like cellulosics such as CMC, chitosan, pectin, guar gum, starches or dextrines, collagenes and gelatine and synthetic polymers like polyacrylic acid, polyvinylealcohol/acetate, polyhydroxy-alkyl acrylates and methacrylates, polyacrylamides, polystyrene sulfonates, polyvinyl pyrilidone, polyglycols, copolymers, grafts of such, copolymers or compositions of such.

The adhesive of the central portion of the dressing may be any suitable skin-friendly adhesive.

The skin-friendly adhesive may be any skin-friendly adhesive known per se for production of medical articles, which are to be adhered to human skin, preferably an adhesive comprising hydrocolloids or other moisture absorbing constituents for prolonging the time of use. The adhesive may suitably be of the type disclosed in U.S. Pat. Nos. 4,231,369, 4,367,732, 4,867,748, and 5,714,225. Especially preferred are the adhesives disclosed in U.S. Pat. Nos. 4,367,732, and 5,714,225.

The dressing of the present invention may in one embodiment of the invention be in the form of a mono-phase adhesive, i.e. made from one adhesive component or in accordance with another embodiment of the invention be in the form of a two-zone adhesive, e.g. of the general type disclosed in U.S. Pat. No. 5,714,225, i.e. a part of or all of the adhesive areas of the dressing having maximum thickness being constituted by more than one type of adhesive.

The dressing of the present invention may consist of a backing layer and a layer of adhesive. Such dressing solely consists of backing layer and adhesive layer, any non-adhesive absorbent layer such as a foam pad, gauze or the like is absent. Absorbent properties of the dressing relates to the presence of an absorbent adhesive in the dressing. The adhesive layer may comprise one adhesive or it may be in the form of two or more adhesives, such as one adhesive for the border portion and another adhesive for the central portion.

The interconnected cavities of the central portion may facilitate a liquid distribution effect, allowing liquid in one area to spread to another area of the central portion. The spreading of fluid in the network of cavities may be carried out by mere flow of liquid, a capillary effect or by applying external pressure such as the user rubbing a finger over the dressing during application, or a combination thereof. Hereby, the exudate is distributed over a larger surface area of the adhesive and the zone of contact between the exudate and the adhesive is increased. The initial absorbent capacity of absorbent adhesives is a function of the surface area and thus a faster absorption is achieved when a larger surface gets in contact with the liquid. Theoretically, the spreading of the fluid may enhance the risk of maceration of the underlying skin, but surprisingly it has been shown that the enhanced absorption together with the non-skin contacting areas of the cavities minimizes the risk of maceration and will provide moist wound healing conditions.

When the dressing of the invention is applied to for example a bleeding wound, the droplet of blood being on top of the wound will be distributed into the cavities. The wound contacting surface of the dressing, being the border portion and the adhesive dots being located in between the cavities, will contact and adhere to the skin, without being disturbed by the blood.

Thus, the cavities may be able to store excessive liquid until the adhesive is capable of absorbing it, without the excessive liquid compromising the attachment of the wound dressing by wetting the adhesive surface contacting the skin.

The interconnected cavities of the central portion are in the form of indentations or embossments in the skin-facing adhesive surface forming a pattern of skin-contacting adhesive zones, e.g. dots, separated by the embossed cavities. The skin-contacting adhesive zones may be in the form of discrete zones, surrounded by the cavities. The adhesive zones may have geometrical configurations such as circles, triangles, polygons etc. or they may have a more random configuration. Thus, the skin-facing surface of the central portion comprises discrete adhesive skin-contacting zones separated by non-skin-contacting interconnected cavities. The skin-contacting adhesive zones provide absorption capacity for absorption of wound exudates as well as they serve as a spacer, preventing the cavities from collapsing.

By cavities is herein meant indentations or embossed areas in the adhesive layer in the form of one or more zones where the adhesive layer is thinner than the adhesive layer or where the adhesive layer is absent, thus providing a three-dimensional volume void volume. The skin-facing adhesive surface of the wound dressing is interrupted at the cavities, thus there is not direct contact between adhesive and skin/wound in these cavities. The cavities may be embossed in the skin facing adhesive surface of the wound dressing. These cavities may act as reservoir chambers for the wound fluid and may distribute fluid across a wider area.

The cavities may be in the form of interconnected reservoirs or channels. The cavities may be arranged in an interconnected geometric pattern or it may be in the form of a random pattern.

The central portion of the wound dressing is surrounded by a border portion without cavities, thus it is a continuous skin-contacting layer. The border portion, being without cavities or other interruptions, may serve as a sealing line preventing leakage from the central portion and thus serve as a stop layer as well as it ensures good adhesive tack to the skin. Such continuous layers provide no channels for liquid to escape from the central portion of the wound dressing. The border portion may constitute 10-50%, such as 15-45%, such as 17-40% such as 20-40% of the area of the dressing. The border portion may have a width of 2.5-25 mm; more preferred 3-20 mm.

The backing layer may be any layer or film being water impervious but vapor permeable. The backing layer may be of any suitable material known per se for use in the preparation of wound dressings e.g. a foam, a non-woven layer or a polyurethane, polyethylene, polyester or polyamide film.

An especially suitable material for use as a backing layer is a polyurethane film. A preferred low friction film material is disclosed in U.S. Pat. No. 5,643,187.

The continuous border portion may be bevelled by having the outer periphery of the dressing having a decreased thickness. The bevelled portion may provide a smoother transition between the dressing and the skin and reduce the risk of "rolling-up" the edge of the dressing thereby reducing the wear-time. The outer periphery of the dressing may preferably be bevelled in analogy with the disclosure of U.S. Pat. No. 4,867,748 or U.S. Pat. No. 5,133,821. The edge is preferably bevelled so that the thickness adjacent to the edge does not exceed about 30% of the maximum thickness of the dressing; more preferred not exceeding 25% of the maximum thickness.

The thickness of the adhesive layer of the central portion may preferably be at least 0.5 mm, more preferred 0.5-2 mm and even more preferred 0.6-1.6 mm. The thickness of the adhesive layer is measured at the point where the adhesive layer is thickest and without cavities, thus the thickness is the distance from the skin contacting surface to the backing layer, measured perpendicular to the backing layer. The adhesive layer may preferably have the same thickness over the entire central portion, apart from the indentations/cavities.

The thickness of the adhesive of the border portion may be the same as the thickness of the centre portion or it may be thinner. The interface between the central portion and the border portion may be beveled in order to facilitate a smooth transition. In one embodiment, the thickness of the border portion is 0.05 mm-0.4 mm, more preferred 0.05-0.2 mm, even more preferred 0.05-0.1 mm.

In one embodiment, the area of the cavities constitutes at least 20% of the area of the skin-facing surface of the central portion. In one embodiment the cavities constitutes at least 25%, such as at least 30%, such as at least 40%, such as at least 50%, such as at least 60% such as at least 70% of the skin-facing surface of the central portion.

The depth of the cavities, measured from the skin-facing surface to the bottom of the cavity, may be substantially the same as the thickness of the adhesive layer, leaving the backing layer above the cavity without adhesive or with only a thin layer of adhesive. In one embodiment, the depth of the cavities is smaller than the thickness of the adhesive layer, leaving a thinner layer of adhesive on the backing layer in the cavities. The depth of the cavities may be at least 75%, such as at least 50%, such as at least 40% such as at least 30%, such as at least 20% of the adhesive layer. In one embodiment the depth of the cavities is 0.3-0.5 mm.

The cavities may be defined as three-dimensional structures defined by the skin as bottom wall, the backing layer as top wall, the backing layer optionally being coated with a thin adhesive layer as the top wall, and edge portions of the adhesive as side walls. The cavities may have a width of 0.1-1 mm, such as 0.1-2 mm, such as 0.1-0.5 mm, such as 0.5-1 mm, such as 0.5-2 mm, such as 0.5-3 mm, such as 0.5-4 mm, such as 1-3 mm, such as 1-4 mm, the width being measured at the most narrow point between the skin contacting adhesive zones of the centre portion.

The transition line between the central portion and the border portion may be in the form of an embossed channel being interconnected to the cavities. The channel may serve as an extra protection against leakage. The channel may encirculate the central portion.

Apart from handling exudates, the cavities may provide shock absorbent properties, providing pressure relief due to an "air-bag" effect from the air-filled cavities.

Furthermore, whereas a traditional continuous hydrocolloid adhesive dressing may enhance the thickness in the areas where moisture is absorbed, due to vertical absorption by the hydrocolloids, the dressing of the invention may show less increase in thickness as the hydrocolloid adhesive may be able to expand horizontally.

EXPERIMENTAL

A test was performed in order to show the exudates handling properties of the dressing of the invention compared to a state-of-the-art dressing with a continuous adhesive skin-contacting surface.

Sample A was a dressing in the form of a polyurethane backing layer coated with a continuous layer of hydrocolloid adhesive, representing state-of-the-art. The dressing was 9.6×9.6 cm and had a thickness of 1.0 mm.

Sample B was a dressing according to the invention, in the form of a polyurethane backing layer coated with a layer of hydrocolloid adhesive, the dressing comprises a central portion, and an border portion surrounding the central portion, the skin facing surface of edge portion of the adhesive layer is continuous and the skin facing surface of central portion is interrupted by interconnected cavities as shown in FIG. 1. The dressing was 9.6×9.6 cm and had a thickness of 1.0 mm and the cavities were 0.25 mm deep. The cavities comprise 57% of the skin-facing surface of the central portion. The border portion had a width of 10 mm.

The samples were applied to a siliconized glass plate, imitating the skin surface, and 0.9 ml artificial wound exudates (colored water) were injected through a hole in the glass plate under the dressing, to simulate a bleeding or exuding wound. Then a roller was passed over the samples to exert pressure to the dressing.

Results:

Sample A: The injected exudates formed a bubble of liquid under the central portion of the dressing, and when pressure was applied to the dressing by the roller, the liquid splashed over the skin-contacting surface of the dressing and escaped under the border portion of the dressing.

Sample B: The injected exudates were distributed in the cavities around the injection point of the dressing and when pressure was applied, the liquid was further spread out into the cavities of the dressing. No liquid escaped under the border of the dressing, the entire amount of exudates was trapped in the cavities.

DETAILED DESCRIPTION OF THE DRAWINGS

Figure 1:
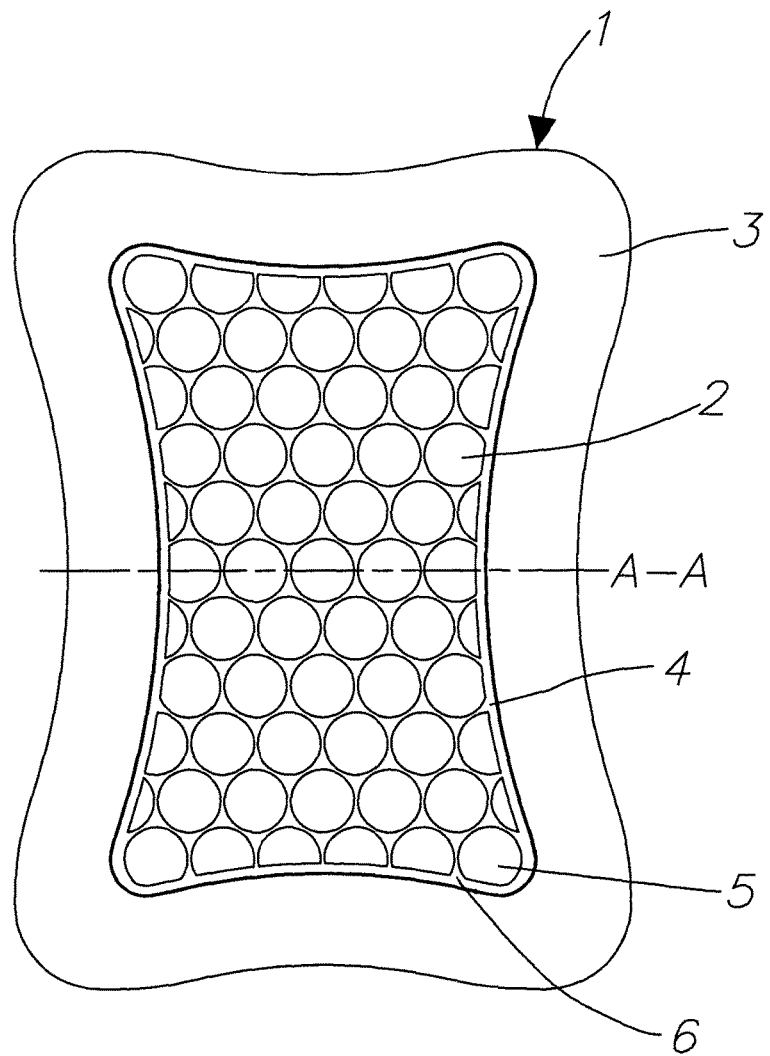
FIG. 1 shows an embodiment of the invention seen in perspective.

The invention will now be described in further detail with reference to the figures. FIG. 1 discloses a preferred embodiment of the invention in the form of an adhesive wound dressing (1) comprising a central portion (2) surrounded by a border portion (3). The central portion comprises a network of interconnected cavities (4) between dots (5) of adhesive. Along the transition zone between the central portion (2) and the border portion (3) is a channel (6), connected to the cavities (4).

Figure 2:
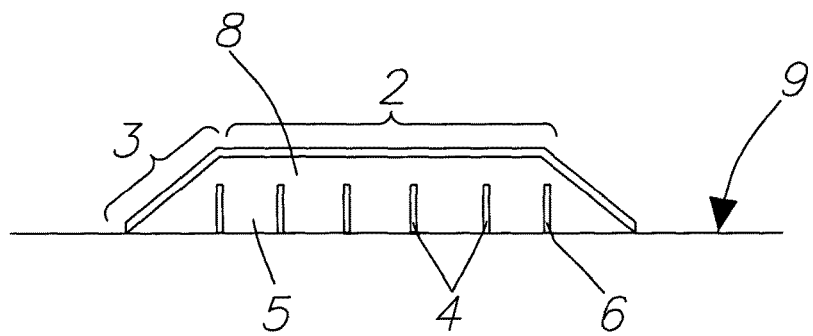
FIG. 2 shows a cross-section of the dressing.

In FIG. 2 is shown a cross-section of the dressing along the A-A line in FIG. 1, disclosing a backing layer (7), facing away from the skin surface (9) and coated on the skin facing surface with an adhesive layer (8). In the skin facing surface are embossed cavities (4) with discrete adhesive zones (5).

The invention claimed is:

1. A wound dressing comprising an adhesive layer having a skin-facing surface and a non-skin-facing surface, the non-skin-facing surface being provided with a backing layer, the adhesive layer comprises a central portion comprising an absorbent adhesive and an adhesive border portion surrounding the central portion, the skin facing surface of border portion of the adhesive layer is continuous and wherein the skin facing surface of central portion comprises discrete adhesive skin-contacting zones separated by non-skin contacting interconnected cavities.

2. A dressing according to claim 1, wherein the absorbent adhesive layer comprises hydrocolloids.

3. A dressing according to claim 1, wherein the continuous border portion is 2.5-20 mm wide.

4. A dressing according to claim 1, wherein the backing layer is a polyurethane film.

5. A dressing according to claim 1, wherein the continuous border portion is beveled between an outer periphery of the dressing and the central portion.

6. A dressing according to claim 1, wherein a thickness of the adhesive layer of the central portion is at least 0.5 mm.

7. A dressing according to claim 1, wherein an area of the cavities constitutes at least 20% of an area of the skin-facing surface of the central portion.

8. A dressing according to claim 1, wherein a depth of the cavities is at least 20% of a thickness of the adhesive layer.

9. A dressing according to claim 1, wherein a depth of the cavities is substantially the same as a thickness of the adhesive layer.

10. A dressing according to claim 1, wherein the cavities are interconnected in a geometric pattern.

11. A dressing according to claim 1, wherein the cavities are interconnected in a random pattern.

12. A dressing according to claim 1, wherein the dressing is adapted to be placed over skin of a user such that the cavities are adapted to be positioned adjacent to the skin, wherein the cavities are then defined by the skin as bottom wall, the backing layer as a top wall, and edge portions of the absorbent adhesive as side walls when the dressing is positioned over the skin of the user.

13. A dressing according to claim 1, wherein the adhesive of the border portion is the same adhesive as the absorbent adhesive of the central portion.

14. A dressing according to claim 1, comprising a transition zone between the central portion and the border portion, with a channel formed in the transition zone and connected to the interconnected cavities.

* * * * *